US008171937B2

(12) United States Patent
Bendett et al.

(10) Patent No.: US 8,171,937 B2
(45) Date of Patent: May 8, 2012

(54) METHOD AND APPARATUS FOR PRECISION WORKING OF MATERIAL

(75) Inventors: Mark Bendett, Ann Arbor, MI (US); Mark Bischoff, Riechheim (DE); Mario Gerlach, Eisenberg (DE); Dirk Muehlhoff, Kunitz (DE)

(73) Assignee: Carl Zeiss Meditec AG, Jena (DE)

( * ) Notice: Subject to any disclaimer, the term of this patent is extended or adjusted under 35 U.S.C. 154(b) by 3 days.

(21) Appl. No.: 12/012,405

(22) Filed: Feb. 1, 2008

(65) Prior Publication Data

US 2008/0147052 A1    Jun. 19, 2008

Related U.S. Application Data

(63) Continuation of application No. 10/625,157, filed on Jul. 23, 2003, now Pat. No. 7,351,241.

(60) Provisional application No. 60/475,583, filed on Jun. 2, 2003.

(51) Int. Cl.
*A61B 19/00* (2006.01)

(52) U.S. Cl. ............................................. 128/898; 606/3

(58) Field of Classification Search ............... 606/3–6, 606/8, 9–12, 166; 607/88–92; 128/898
See application file for complete search history.

(56) References Cited

U.S. PATENT DOCUMENTS

| | | | |
|---|---|---|---|
| 4,907,586 A * | 3/1990 | Bille et al. ........................... | 606/5 |
| 5,129,895 A * | 7/1992 | Vassiliadis et al. ................ | 606/6 |
| 5,656,186 A | 8/1997 | Mourou et al. | |
| 5,738,677 A | 4/1998 | Colvard et al. | |
| 5,984,916 A | 11/1999 | Lai | |
| 5,993,438 A * | 11/1999 | Juhasz et al. ....................... | 606/5 |
| 6,110,166 A | 8/2000 | Juhasz | |
| 6,146,375 A | 11/2000 | Juhasz et al. | |
| 6,325,792 B1 | 12/2001 | Swinger et al. | |
| 6,552,301 B2 | 4/2003 | Herman et al. | |
| 6,805,694 B2 | 10/2004 | Donitzky | |
| 6,872,202 B2 | 3/2005 | Gerlach et al. | |
| 7,131,968 B2 | 11/2006 | Bendett et al. | |
| 7,351,241 B2 * | 4/2008 | Bendett et al. ..................... | 606/5 |
| 2005/0107773 A1 * | 5/2005 | Bergt et al. ........................ | 606/4 |

FOREIGN PATENT DOCUMENTS

| | | | |
|---|---|---|---|
| DE | 197 27 573 | | 5/1998 |
| DE | 197 46 483 | | 5/1999 |
| DE | 10202036.1 | * | 1/2002 |
| WO | 01/54853 | | 8/2001 |
| WO | WO 03/059563 | * | 1/2003 |

OTHER PUBLICATIONS

*Optics Letters*, vol. 26, No. 11 (2001), K. König et al.
Electronics Letters 29, 1666-1667 (1993), "Room temperature operation of a sub-micron radius disk laser" Levi, et al.
Captain Massey "High-Power, High-Efficiency Spinning Disk Laser" DE-04-02.

* cited by examiner

*Primary Examiner* — Ahmed Farah
(74) *Attorney, Agent, or Firm* — Frommer Lawrence & Haug LLP

(57) ABSTRACT

A method for precise working of material, particularly organic tissue, comprises the step of providing laser pulses with a pulse length between 50 fs and 1 ps and with a pulse frequency from 50 kHz to 1 MHz and with a wavelength between 600 and 2000 nm for acting on the material to be worked. Apparatus, in accordance with the invention, for precise working of material, particularly organic tissue comprising a pulsed laser, wherein the laser has a pulse length between 50 fs and 1 ps and with a pulse frequency of from 50 kHz to 1 MHz is also described.

20 Claims, 5 Drawing Sheets

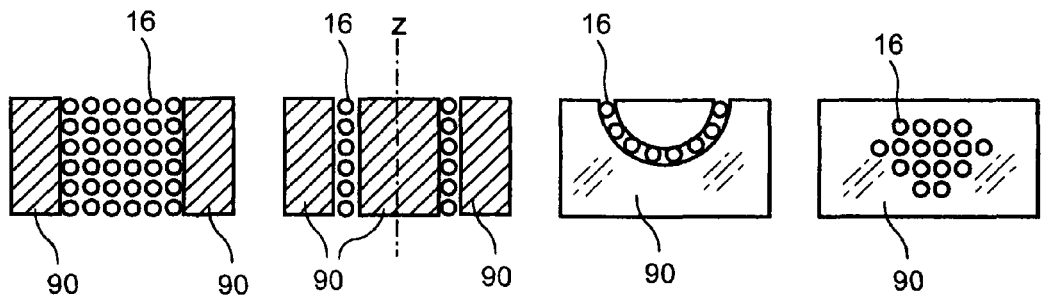
F I G. 3A  F I G. 3B  F I G. 3C  F I G. 3D
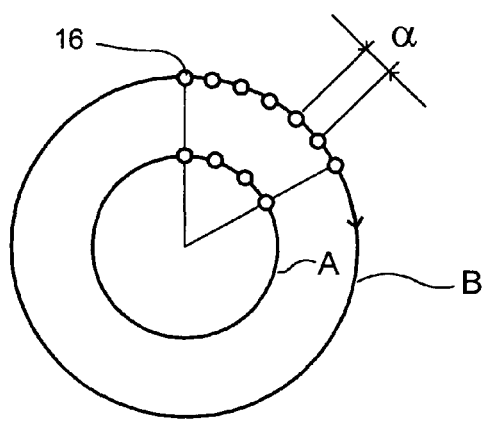
F I G. 4
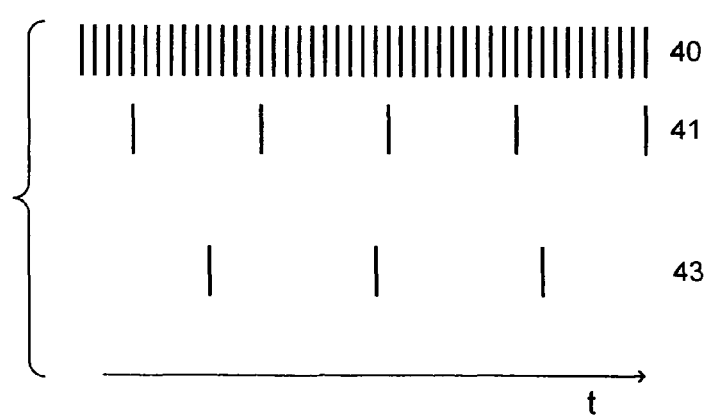
F I G. 5

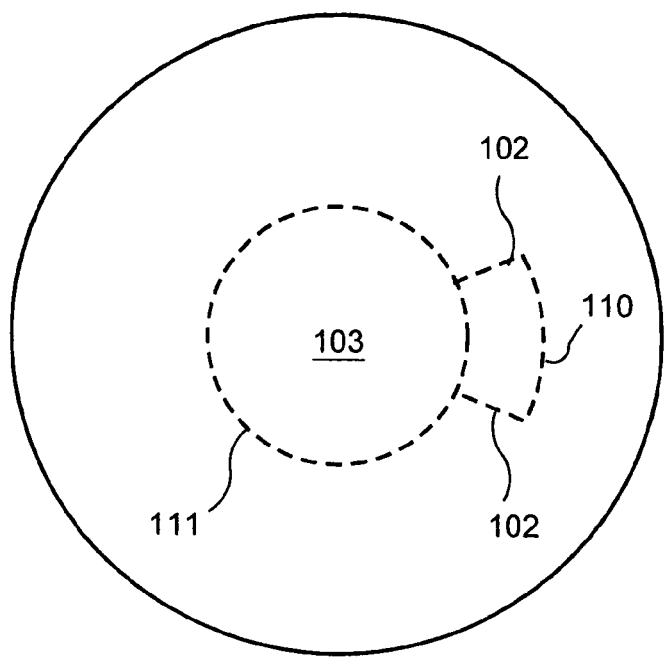
F I G. 8
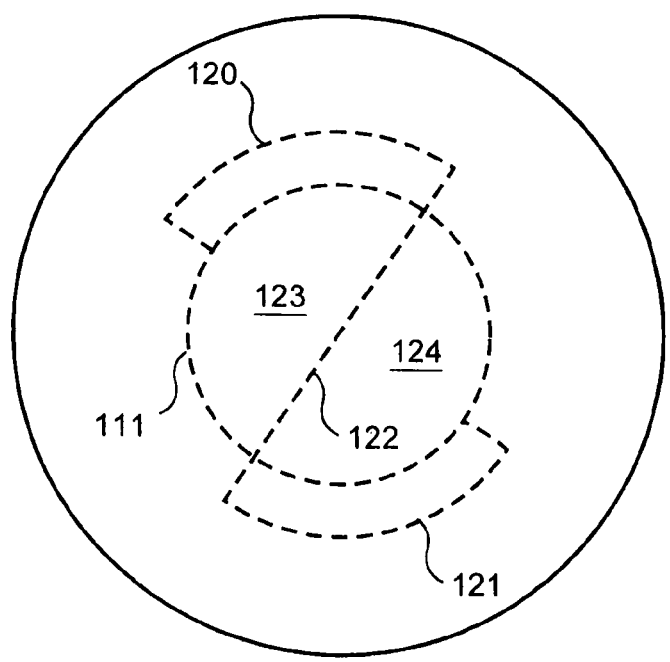
F I G. 9

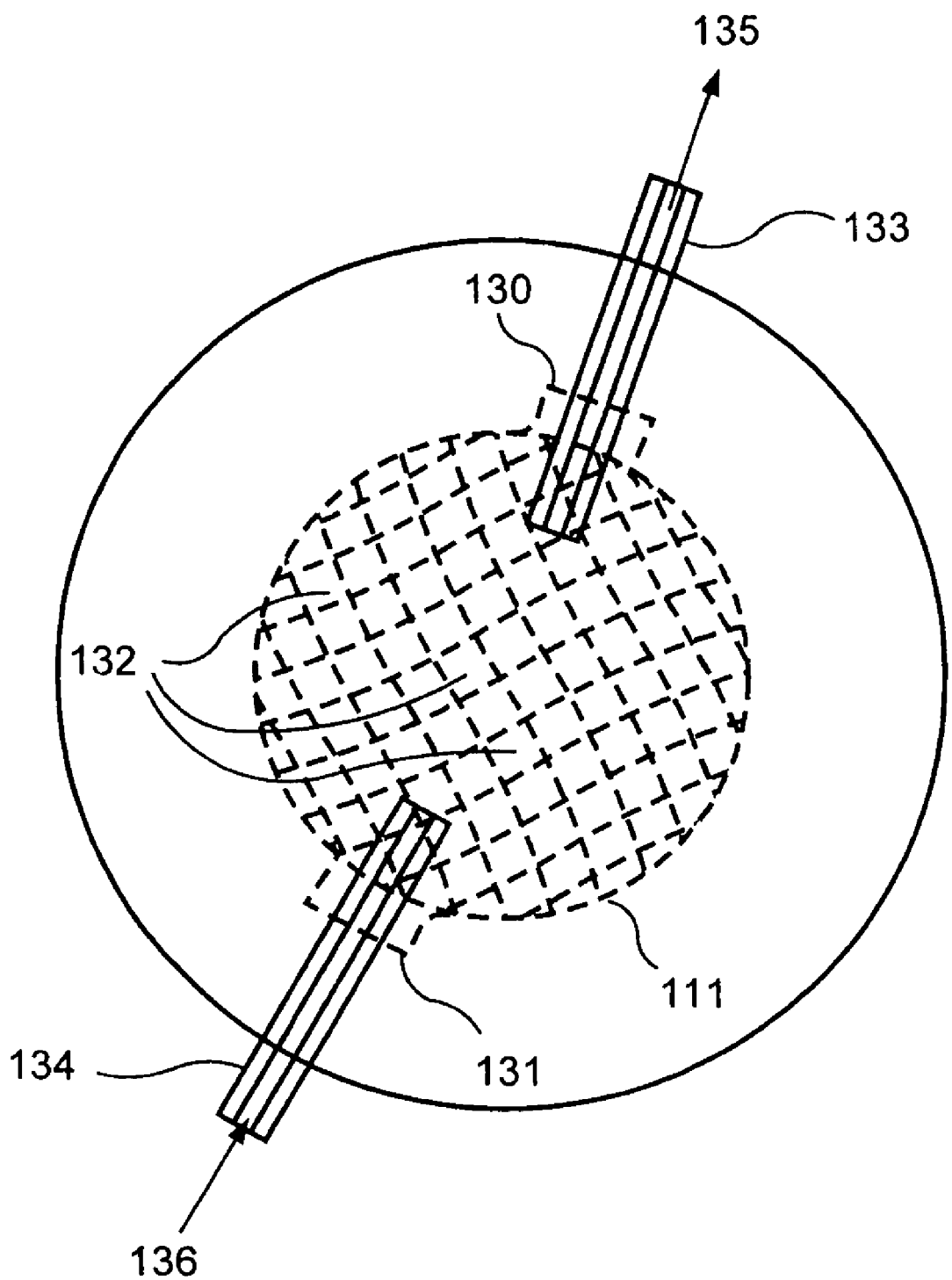
F I G. 10

METHOD AND APPARATUS FOR PRECISION WORKING OF MATERIAL

CROSS-REFERENCE TO RELATED APPLICATION

This application is a Continuation Application of application Ser. No. 10/625,157, filed Jul. 23, 2003 now U.S. Pat. No. 7,351,241, which claims the priority of U.S. Provisional Application No. 60/475,583, filed Jun. 2, 2003, the complete disclosure of which is hereby incorporated by reference.

BACKGROUND OF THE INVENTION a) Field of the Invention

The invention is directed to a femtosecond laser system for precise working of material and tissue, particularly a laser device for the precise, micrometer-exact working of organic material, preferably an eye.

b) Description of the Related Art

In a valuable contribution to the art, German Patent DE 197 46 483 by the present Applicant describes how macroscopic amounts of material are ablated, vaporized or melted ($CO_2$ laser, Nd:YAG, excimer . . . ) with micrometric precision when working over large surface areas of materials by means of lasers with large spot diameters.

In another valuable contribution to the art, German Patent DE 197 27 573 by the present Applicant describes an algorithm by which a laser beam can be deflected in order to ensure the best possible, most precise working of material.

U.S. Pat. No. 5,656,186 describes a method for working material while simultaneously preventing or minimizing damaging side effects (melting edges, thermal damage, acoustic shock waves, cracking) through the selection of a special pulse duration depending on the material.

The material-working action of the laser is limited to the small spatial area of the laser focus (typically a few $\mu m^3$) in which the light intensity is high enough to exceed the threshold of optical breakdown. Localizing on the focus volume, the cohesion of the material is destroyed and a cavitation bubble is formed. When the laser focus is directed to a new position for every laser pulse, linear, flat or three-dimensional cut patterns can be generated. The distance between adjacent cavitation bubbles at the conclusion of the operation must approximately correspond to their diameter so that the material can easily be removed mechanically along the cuts.

Existing laser instruments for working materials with femtosecond laser pulses use regenerative amplifiers with repetition rates of up to 15 kHz by which individual pulses of a femtosecond oscillator are amplified. While the oscillator itself only provides pulse energies in the nanojoule range, the pulses can be amplified up to several millijoules by a regenerative amplifier. While these laser sources are suitable for applications with high ablation rates per laser pulse, they are not optimal for the above-described application for precision cuts.

It is known to use lasers of the type mentioned above for refractive cornea surgery. Usual pulse energies are 5 $\mu$J to 10 $\mu$J. Cavitation bubbles with diameters of 10 $\mu$m to 30 $\mu$m are generated in this way. These bubble dimensions cause a micro-roughness of the generated cut on the same order of magnitude. On the other hand, it is known that a micro-roughness on this order of magnitude allows only unsatisfactory refractive results.

K. König et al., *Optics Letters*, Vol. 26, No. 11 (2001) describes how cuts in tissue can also be carried out with nanojoule pulses from a femtosecond oscillator. However, due to the fact that an individual laser pulse does not lead to formation of a cavitation bubble but that, rather, a plurality of pulses placed at the same location are needed to generate a cutting action, this method is only suitable for very fine cut shapes on the micrometer scale. This laser source is not suitable for industrial or medical use.

OBJECT AND SUMMARY OF THE INVENTION

Therefore, it is the primary object of the present invention to provide an apparatus for precise working of material which overcomes the disadvantages of the prior art.

In particular, the above-stated object is met by an apparatus for precise working of material, particularly organic material. This apparatus generates cavitation bubbles with a diameter of less than 10 $\mu$m in the material to be worked. In order to achieve this, a pulsed laser beam with a pulse energy of less than 5 $\mu$J is focused on a focus diameter of a few micrometers. The focus diameter is preferably about 3 $\mu$m and the pulse energy is preferably 1 $\mu$J. Further, the apparatus is characterized in that it permits very fast working through the use of a pulse repetition rate of greater than 50 kHz. This is a great advantage particularly for refractive cornea surgery because an operating time of a few seconds to about 1 minute is achieved in this way.

The object is further met by an apparatus for precise working of material, particularly organic material, comprising a pulsed laser system with the above-described parameters as radiation source in which a work beam of the radiation source can be applied to the material by means of a beam device with at least one device for beam deflection. The pulse emission is correlated with the beam deflection and the device for beam deflection comprises means for enabling laser pulses. By enabling is meant that the laser is enabled for a laser pulse and the laser pulse is triggered as soon as the laser is again able to deliver a laser pulse corresponding to its maximum repetition rate. When it is stated that the pulse emission is correlated with the beam deflection, this means in particular that the pulse emission can be carried out when the beam has been directed to a determined point; that is, the pulse emission is controlled depending on the beam deflection.

In a special construction, the above-stated object is met through an apparatus for precise working of material, particularly organic material, comprising a pulsed laser system as radiation source. The beam energy is about 100 nJ to 10 $\mu$J, preferably 500 nJ to 5 $\mu$J. The repetition rate of the radiation is preferably 50 kHz to 1 MHz, particularly preferably 100 kHz to 500 kHz. The focus diameter of the beam is preferably about 500 nm to 10 $\mu$m, particularly preferably 3 $\mu$m to 5 $\mu$m. The pulse duration of the radiation is preferably about 100 fs to 1 ps, particularly preferably 200 fs to 500 fs.

The arrangement for beam shaping and/or beam deflection or, generally, the beam-shaping and beam-deflection systems can comprise diffractive or refractive microoptics or adaptive optics or conventional optical systems. A number of conventional optical elements can be replaced by diffractive or refractive elements.

The apparatus mentioned above for precise working of material is preferably used for opthalmologic eye treatment, particularly for correcting visual deficiency of an eye. The apparatus can be used to cut a flap or lenticle in the cornea for correcting visual deficiency. In addition to cutting the lenticle, the apparatus according to the invention can also generate refractive structures in the cornea, for example, in the form of flat spots placed side by side or a point cloud.

Laser shots can also be applied directly for generating refractive structures. For example, small bubbles can be generated in the lens of the eye by evaporating material or liquid. A great many comparatively low-energy laser shots such as can already be carried out with the apparatus according to the invention are required for this purpose.

It is likewise possible to introduce deliberate cuts in the tissue, for example, the eye lens, with the apparatus according to the invention and, therefore, to improve the flexibility and elasticity of the lens, since the adjacent tissue portions can now be displaced relative to one another more easily. The apparatus for precise working of material, particularly organic material, is used in this construction of the invention as an apparatus for the treatment of presbyopia. The beam shaping is carried out either conventionally or with diffractive or refractive microoptics or adaptive optics. The beam deflection is preferably carried out by means of scanning systems.

Suitable laser beam sources are oscillator-amplifier arrangements. Suitable amplifiers are particularly regenerative amplifiers, chirped pulse amplifiers (CPA) or multipass amplifiers.

With respect to the constructional form of the mode-coupled oscillator, disk laser oscillators, fiber laser oscillators, and rod laser oscillators are particularly suitable. As regards the constructional form of the amplifier, disk laser amplifiers, fiber laser amplifiers, and rod laser amplifiers are particularly suitable.

Semiconductor laser diodes are particularly preferred as a pump source for the laser media due to their long life, dependability, controllability and their comparatively low manufacturing costs.

Preferred laser media in the above-mentioned laser beam sources are doped solid state materials, particularly crystals and glasses. Examples are YAG, tungstate, sapphire and fluoride glass.

These host materials can preferably be doped with neodymium, erbium, titanium, chromium, lithium or ytterbium. All of these materials are characterized by a spectrally broadband laser emission in the spectral range of 600 nm to 2000 nm and accordingly comprehend the spectral region between 800 nm and 1200 nm which is particularly suitable for refractive cornea surgery.

The large spectral bandwidth of the laser emission of the above-mentioned materials supports an ultrashort laser pulse duration between 50 fs and 1 ps. In this respect, it is not necessary for the laser itself to emit pulses of this pulse duration, but the preferred pulse duration of about 300 fs can be achieved in the workpiece to be worked or on the surface thereof. For this purpose, the apparatus comprises an optical module which serves to influence the spectral phase function of the laser pulses in a suitable manner. In particular, this optical module generates a linear prechirp whose quantity is adapted to the linear chirp of the optical system. This optical module can already be suitably integrated in a laser beam source; in particular, it can be combined with or be identical to the pulse compressor of a CPA laser beam source.

The material which is preferably to be worked with micrometer precision can comprise material with structures in the micrometer range, gratings, contact lenses, plastics, intraocular lenses (IOL), semiconductor wafers, microoptic elements, etc. Organic material such as tissue is particularly preferred, especially the tissue of the human eye.

The pulsed laser system is an arrangement of a laser beam source for generating fs pulses and corresponding optical apparatus, particularly mirrors, lenses, etc.

In a construction of the apparatus according to the invention, the means for beam deflection are operated in scan mode. The work beam of the radiation source can be deflected on paths which recur periodically in one dimension, so that circular paths of different diameter or spiral paths can be generated, for example. The paths of the work beam can be generated by rotating apparatus or apparatus which can be kept on a path in some other way, for example, by means of a mirror, a lens, a grating or the like. The means for beam deflection can comprise scanners, e.g., mechanical scanners, which are supported so as to be movable on predetermined paths. The present invention uses fast deflection systems which deflect the laser on the natural paths of the deflection system, that is, e.g., on circular paths or spiral paths in rotating deflection systems. Instead of approaching individual positions and triggering a laser pulse there as soon as the given position is reached, whereupon the deflection system is at rest again, the path of the deflection system is traversed without stopping and the pulses are emitted beginning at a defined time with a preselected repetition rate which is given by the path speed of the focusing movement.

As soon as the focus position has reached a determined point, the laser is enabled and laser pulses are accordingly sent to the work area. This results in a track of working volumes, places in the material that are modified by the laser focus during the short pulse duration, along a substantially predefined path which is characterized in particular in that adjacent working volumes are placed at uniform, predefined distance, e.g., on the order of magnitude of the diameter of the cavitation bubbles. Additional tracks which together make up an incision surface can be written through a slight modification of the natural path of the deflection system, e.g., through a slight reduction in the circular path radius, for example, by an amount corresponding to the distance between adjacent working volumes. For instance, concentric paths, spiral paths or the like can be generated. When a deflecting mirror is used, this can be carried out, for example, by changing the inclination while maintaining the same rotation of the mirror. The aim is to cover the desired cut surface with a uniform grid of working volumes or laser foci. The natural paths of the deflection system can be traversed very quickly with a defined time sequence due to the high repetition rate of the laser system. Adapting the time sequence of the laser pulses then results in the desired coverage of the cut surface with laser shots.

Further, beam devices for beam shaping and/or beam control and/or beam deflection and/or beam focusing are provided in another embodiment example of the present invention. By means of these beam devices, the beam can be directed and conducted to the material to be worked as precisely as required in the intended application. Particularly because of their low pulse energy of about 1 µJ, the ultrashort laser pulses which are focused on a focus diameter on the order of magnitude of 3 µm can undo the material coherence and/or bring about structural changes in the material in a small, precise cavitation bubble without thermal, acoustic or mechanical loading of adjacent areas in the material. For macroscopic cuts and structures in the centimeter scale, the laser focus is scanned in a three-dimensional manner through the material to be worked. The specific application determines how the beam source, beam control and beam shaping, scanner, scan algorithm and focusing optics are to be adapted to one another in order to achieve a high working speed with high precision at the same time.

The beam shaping is preferably carried out by means of a telescope (preferably a Galileo telescope with collecting lens and diverging lens) which expands the beam diameter in such a way that the laser can be focused on a corresponding small focus. A lens system which extensively minimizes the imaging error of the telescope is preferably used.

The beam control is preferably carried out by mirrors or pairs of mirrors by which the beam can be adjusted in the individual subcomponents.

The beam deflection arrangement can comprise conventional scanners or mechanical laser beam deflection systems such as galvanometer mirrors in closed-loop mode, etc. However, mechanical scanners which travel given paths (e.g., circular paths) and are accordingly triggered by triggering the beam source at the provided positions are preferable. In this way, a large area of the cut surface can be worked at full repetition rate with relatively slow scanner movements.

The beam focusing device serves to cancel the coherence of the material (photodisruption) in the focus of the beam on or in the material. This is generally accompanied by local vaporization of the material. The laser is preferably focused on a diameter in the micrometer range for this purpose. This is close to the diffraction limit of light in the visible and near infrared range. Therefore, the focusing optics preferably have a high numerical aperture and accordingly a short focal length and a large optical aperture (expanded laser beam diameter). The beam proceeding from the laser source is preferably expanded in diameter before focusing on the material or tissue. The systems for beam control, beam deflection and beam focusing are therefore preferably designed for a large beam diameter.

The laser source, beam deflection (scanner) and focusing optics are so adapted to one another that a precise, fast cutting is made possible by way of photodisruption. Laser spots with a focusing diameter of some 100 nm to several micrometers are placed in the material with a spot distance on the order of magnitude of the cavitation bubble diameter.

In a particularly preferred embodiment form, the beam devices, particularly the deflection devices, are programmable. Due to the ability to adapt the individual beam devices to one another and to control through corresponding programs, the system of beam devices together with the pulsed laser system can be adjusted exactly to the material, and cutting requirements for which it is to be employed. Accordingly, the set of parameters is preselected by the program and adapted depending upon the transparency and refractive power of the material to be worked and upon the required cut geometry and duration of operation.

In another preferred embodiment form of the present invention, holding devices are provided for positioning and/or fixating the material to be worked. These holding devices ensure that the micrometer-exact structures which can be produced by the laser according to the invention are not impaired by uncontrollable movements of the material to be worked, particularly the human eye.

A fixating and positioning device of the kind mentioned above can be a simple clamping device for a workpiece which is preferably outfitted with multiaxial adjusting possibilities for moving and tilting the workpiece for optimal adjustment. Further, fixating devices for medical applications in organs such as the eye must be adapted to the given biological factors. The human eye may be fixated, for example, by means of a special adapter and a vacuum suction ring.

Because of the high repetition rates described above in conjunction with the low pulse energies and the deflection devices described above, the laser action for the photodisruption can be precisely localized. In this way, the material structure can be destroyed in a sharply defined focus volume; in closely adjacent areas (less than one micrometer apart), there is generally no change in the material. This results in high working precision (micrometer accuracy) without damage to adjoining regions of material. Thermal and mechanical loading of the regions that are not worked is appreciably less than in other cutting methods.

In another preferred embodiment form of the apparatus according to the invention, a work beam of the radiation source can be applied to the material by means of the beam device, particularly the deflection device, in a geometrically predefinable shape in a time sequence that can be predetermined. Due to the interplay of the individual components, it is accordingly possible to generate cuts and structuring. One laser pulse with defined pulse parameters (pulse energy, pulse duration, focus) is generally sufficient to produce a spot in which the material structure is dissolved. A plurality of spots of this kind must be placed close together for cuts and structuring. The distance between adjacent spots should be on the order of magnitude of the cavitation bubbles at the conclusion of the procedure. For this purpose, the laser focus can be moved in a scanning manner over and through the material. The laser focus ideally follows a predetermined geometric path in a three-dimensional manner with micrometer accuracy. It is possible, for example, to produce a cut in the material to be worked by moving in a scanning manner over any surface, e.g., a rectangular surface of adjacent micrometer spots, in the tissue one after the other. As a result, the material coherence is dissolved precisely in this plane and a cut is accordingly produced in the tissue. It is also possible to apply the laser focus to the material to be worked by circular movements of the scanner in a circular path. By subsequently guiding the working beam in a helical pattern, a cylindrical surface can be cut out of the material, for example. Since the photodisruption preferably takes place within a very compact area, the laser beam can also act in tissue without damaging the material penetrated by the laser beam outside of the focus. In this way, any geometric paths, and therefore shapes, can be cut out of the material though photodisruption.

In refractive cornea surgery, a special cut guiding can be realized by the apparatus according to the invention. Rather than preparing a traditional flap, the lenticle which is prepared beforehand in the cornea by the apparatus according to the invention is extracted at the circumference by means of one or more defined lateral cuts which are likewise generated by the apparatus according to the invention. For this purpose, it can be advantageous to split the lenticle beforehand by one or more cuts with the apparatus according to the invention. In particular, splitting is useful when the parts are removed subsequently by suction with a suction/rinsing cannula.

In the preferred embodiment example of the present invention, an apparatus is provided in which the pulsed work beam can be applied to the material by the beam deflection device, during which the repetition rate of the pulses of the work beam can be modified. By providing a device for modifying the repetition rate with simultaneous beam control of the work beam over the material to be worked, a uniform pattern of spots can be generated in an elegant manner on the material to be worked, even when the beam is directed to the material to be worked at different angles or different speeds by the deflection device. A particularly striking advantage is achieved, for example, when the deflection device directs the beam in circular paths to the material to be worked and these circular paths are generated with a special rotational frequency of the deflection device, particularly the deflection mirror, for example. At a rotational frequency of 50 Hz, for example, the laser beam is guided on a circular path of 1 cm diameter at a repetition rate of 300 kHz, then 60,000 spots are placed in a uniformly distributed manner on every circular path per revolution. When the beam is guided on a circle with a diameter of only 0.5 cm at the same frequency of the deflection device, the same distance between the individual spots as that produced when guiding the beam on the larger circular path can be produced on the material to be worked by lowering the repetition rate of the pulsed work beam. By correspondingly modifying the repetition rate depending on the geometry followed by the deflection device, any geometric pattern can be generated on the material to be worked with an essentially constant distance between spots. For example, spirals can be traveled in which the repetition rate continuously decreases from the outside to the inside with a uniform rotational frequency of the deflection device. Apart from this, any other geometric shapes are also possible. When a constant distance between the individual spots on the material is not intended but, rather, a higher spot density is to be achieved in a specific area and a lower spot density is to be achieved in another area, this can also be produced by a combination of the selected parameters for the repetition rate of the work beam and the frequency or spatial course of the deflection device. For example, it is also possible in a preferred manner to generate gradually differing areas with different focus densities. In the case of a circle, for example, the center can have a very small focus distance while the focus distance to the edge is increasingly greater.

The object of the invention is also met through a method for applying fs pulses of a laser beam source with the characteristics noted above, particularly high repetition rate and low pulse energy, to a material, particularly an organic material, in particular the human eye, in which the material is worked in the focus of the laser beam by means of photodisruption or its coherence is dissolved.

In a particularly preferred method of the present invention, the pulsed laser beam is directed to the material to be worked by means of a deflection device and the repetition rate of the pulses of the laser beam is modified depending on the spot pattern generated in this manner on the material. In this way, any spot pattern and particularly any distance between the individual spots can be produced in the desired geometry on the material to be worked. In a particularly preferred manner, the spot patterns are distributed on the material to be processed in such a way that the cavitation bubble of every individual spot occurring through photodisruption is placed exactly next to the cavitation bubble of the next spot. A desired cut pattern of directly adjacent cavitation bubbles is formed in this way. For special applications, it can also be desirable to place the spots even closer together. This is recommended, for example, when the material to be worked is renewed again after a certain time and the dissolution of the material is to be ensured for a specific time before, e.g., the drill core or another piece that is cut out of the material to be worked can be removed. It is also possible that the spots are initially placed at a greater distance from one another in order to fill the gaps between the spots in a subsequent step and accordingly to form a desired pattern of cavitation bubbles.

The apparatus according to the invention can be used for refractive surgery by working the cornea or the lens of the eye.

Additional advantageous constructions of the invention will be described in the following with reference to the drawings.

BRIEF DESCRIPTION OF THE DRAWINGS

In the drawings:

FIG. 3 shows a schematic view of some examples of possible cut patterns which can be made with the laser system according to the invention;

FIG. 4 shows a schematic detailed view of a sequence of laser spots on circle lines; and FIG. 5 shows the timeline of sequences of laser pulses in and outside of the laser resonator;

FIG. 8 shows the cut lenticle in a top view of the cornea;

FIG. 9 shows another form of the cutting control in which the lenticle is divided and can be extracted through two lateral cuts; and FIG. 10 shows another embodiment of the method according to the invention, wherein the lens is divided in many parts which are removed by a suction/rinsing device.

DESCRIPTION OF THE PREFERRED EMBODIMENTS

Figure 1:
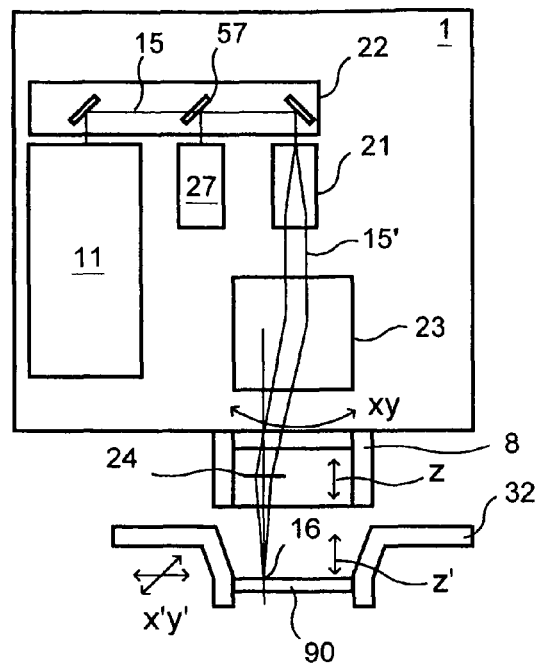
FIG. 1 shows a schematic view of an embodiment example of a laser according to the invention.

FIG. 1 shows a schematic view of the individual components of an embodiment example of a laser system according to the invention. The working device 1 comprises an fs laser beam source as radiation source 11. The laser beam 15 is coupled out to beam expansion optics 21 by mirrors and a beam splitter 57. The expanded laser beam 15' is then guided by a beam deflection device such as a scanner in XY-direction to a beam focusing device 24. The latter is displaceable in the Z-axis and accordingly allows the displacement of the focus point by displacing the beam focusing device along arrow Z. Alternatively, a focusing optical system with variable focal length can be used in order to displace the focus position in Z-direction in a controlled manner. In this way, the focused laser spot 16 is directed onto the material 90 to be worked, which material 90 is held in its position by means of a fixating device 32. In the present instance, the material 90 is a contact lens to be worked. The spot 16 can also be oriented by displacing the fixating device 32 in direction XY' or Z' on or in the material.

The laser beam 15 generated by the radiation source 11 is focused on the material 90 by the working apparatus 1. A focus diameter of a few micrometers can be achieved in that the laser beam 15 is focused with a beam diameter of a few millimeters through optics with a few centimeters focal length. For a Gaussian beam profile, for example, there is a focus diameter of three micrometers when focusing a laser beam of wavelength 1000 nm and a beam diameter of 10 mm with a focal length of 50 mm.

Generally, the diameter of the laser beam 15 at the output of the radiation source 11 is smaller than is necessary for optimal focusing. With beam expansion optics 21, the beam diameter can be adapted to requirements. A Galileo telescope (diverging lens plus collecting lens) which is adjusted to infinity can preferably be used as beam expansion optics 21. There is no intermediate focus in this case which could lead to an optical breakdown in air under certain circumstances. The remaining laser energy is accordingly higher and the beam profile is consistently good. It is preferable to use lens systems which lead to optimal imaging characteristics of the telescope. By adjusting the telescope, manufacturing variations can also be compensated in the beam divergence of the radiation source 11.

In this embodiment example, the laser focus is moved over or through the material in a scanning manner. The laser focus or laser spot 16 is accordingly scanned three-dimensionally with micrometer accuracy. The expanded laser beam 15' is deflected perpendicular to the original beam direction by a deflection device 23. The position of the focus 16 after the focusing optics 24 is displaced perpendicular to the original beam direction. The focus can accordingly be moved in a surface which is essentially plane and perpendicular to the laser beam direction (X/Y direction). The movement parallel to the beam direction (Z-direction) can be carried out on one hand by moving the workpiece (see arrow Z'). The scan algorithms are then preferably configured in such a way that the workpiece need only be moved slowly and the fast scanning movements are carried out by the deflecting unit. On the other hand, the focusing optics can also be moved parallel to the laser beam direction (arrow Z) in order to lower the focus in the Z-direction. Particularly in medical applications, the second method is preferred because the patient can generally not be moved quickly enough.

The worked material 90 is fixated relative to the laser device in a fixating and adjusting device 32. In this connection, the fixating device is preferably adjusted vertical to and parallel to the beam device in order to be able to place the cut pattern at the intended location in the material 90. A visible laser beam which proceeds from a pilot laser 27 and is collinear with the working laser beam 15, 15' supports the adjustment.

Mirrors or pairs of mirrors 22 are provided for beam control and for precision adjustment of the beam position between the individual components. The mirrors are preferably so constituted that the working laser beam does not destroy the mirrors, but the mirrors are highly reflecting for the wavelength of the working laser and are sufficiently reflecting for the pilot laser. The coating is selected in such a way that the mirror does not substantially lengthen the laser pulse duration. In a particularly preferable manner, at least one of the mirrors is a chirped mirror with which the dispersion of all of the optics present in the beam path can be compensated in order to achieve optimally short pulses in the working focus.

Figure 2:
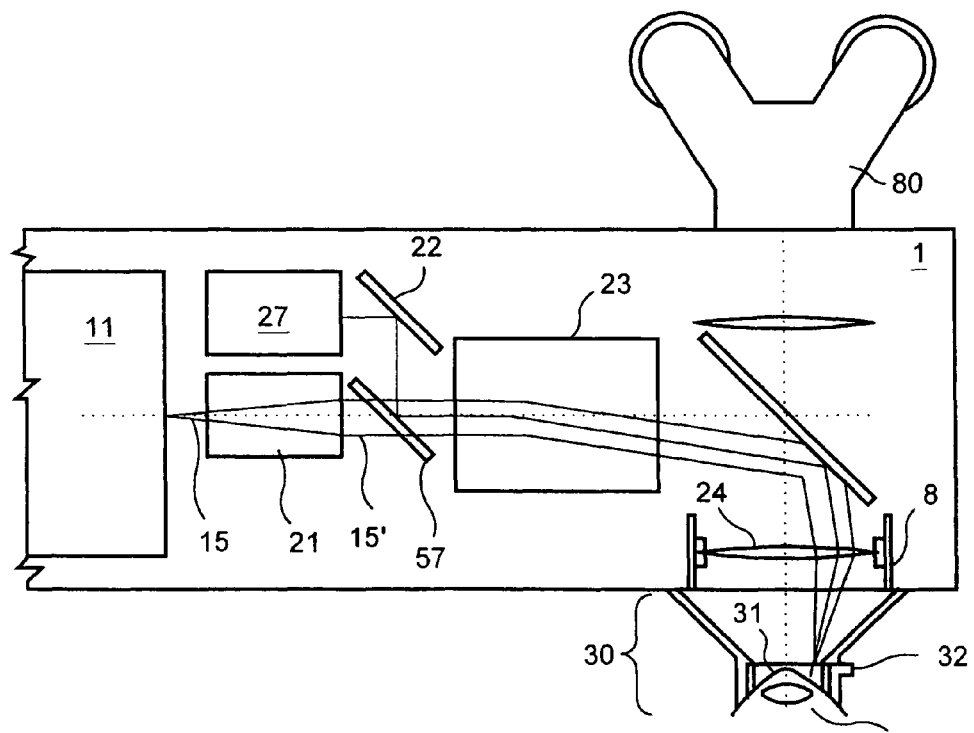
FIG. 2 shows another embodiment example of a laser according to the invention with a surgical microscope and an eye to be worked.

FIG. 2 shows another embodiment example of the present laser working apparatus with surgical microscope. The construction corresponds essentially to the construction in FIG. 1. Identical parts are identified by the same reference numbers. In this example, a human eye is provided as material 90. This laser device, with which precise cuts can be made in the cornea of the human eye, will be described in detail by way of example. A circular surface which follows the curvature of the cornea and is centered with respect to the optical axis of the eye is to be cut inside the cornea with fs laser pulses. A cornea flap is formed from the circular surface to the outside of the cornea by an arc-shaped edge cut and can be opened to the side after the laser cut.

A flap of the kind mentioned above is used to prepare for a LASIK operation in which the thickness of the cornea is changed by laser ablation in such a way that refractive errors of the eye are compensated. Previously, this cut was carried out by a mechanical keratomy which requires a high level of training on the part of the physician and is fraught with risk. In addition, a refractive correction of the cornea can be carried out in the same work step through another curved circular surface which, together with the first circular surface of the flap, surrounds a lenticle that can be removed after opening the flap.

In the special embodiment of the invention, the eye is pressed by means of a suction ring 32 against a contact glass 31 which is either plane or preferably essentially adapted to the curvature of the cornea. The suction ring is fixedly connected with the outlet window of the laser device which provides for a defined position of the cornea relative to the laser focus. The expanded femtosecond laser beam is focused in the cornea by optics 24. A beam splitter which is highly reflective for the laser wavelength and transmits visible light reflects the laser beam in the beam path of a surgical microscope which is used for observing and centering the eye. The focusing optics 24 form a part of the microscope objective. Together with bundling optics, a real intermediate image of the cornea can be generated and can be observed three-dimensionally with the stereo eyepiece 80. The beam deflection unit 23 deflects the expanded laser beam 15 vertical to its propagation direction. Accordingly, the laser focus can be directed to different points in the cornea. The depth of focus can be varied by displacing the focusing optics 23 along the optical axis or by adapting the focal length of the focusing optics.

Circular paths are preferably traveled by the deflecting unit. For cutting the circular surface, the circle radius is reduced from circular path to circular path and the repetition rate is so adapted that a uniform spot distance is maintained. The depth of focus is adapted from circular path to circular path in such a way that the cut follows the curvature of the cornea. To perform astigmatic corrections of eyesight (cylindrical correction), the depth of focus can be moved up and down twice over the course of the circular path, so that a lenticle with a cylindrical lens portion is formed. For the flap edge, the depth of focus is slowly displaced from the base of the flap to the outside of the cornea while the radius remains fixed, so that a cylindrical jacket is formed. The laser beam must be interrupted on an arc-shaped segment of the circles described above in order to leave a hinge at which the prepared flap is held. For this purpose, laser pulses are simply coupled out of the radiation source 11.

The radiation source 11 is a femtosecond radiation source with the parameters described above which is preferably directly diode-pumped and therefore simple and reliable. The emitted laser beam 15 is preferably expanded to a 1- to 2-cm beam diameter by a Galileo telescope. A visible laser beam from a pilot laser 27 is superposed collinear to the expanded laser beam 15 and is then scanned and focused together with the working laser beam. For this purpose, the beam splitter 57 is transparent for the femtosecond laser wavelength and reflecting for the pilot beam.

The many possible cut shapes depend only on the scan algorithms. In principle, a laser device such as that described for a great many applications (for example, for refractive correction of vision) in which cuts or structural transformations are made within the transparent parts of the eye (cornea, lens, vitreous body) and on the nontransparent parts such as the sclera, iris and cilliary body are suitable. Accordingly, the invention by far surpasses existing technologies in universality and precision (avoidance of damage to surrounding tissue) even in this small sub-area of the application.

Application examples of cut geometries which can be realized with the laser system according to the invention are shown in FIGS. 3a to 3d. These applications are only given by way of example; any other geometries can be realized. The coherence of the material 90 is canceled (photodisruption) in the focus 16 of the laser. In general, this is brought about by a local vaporization of the material. After the action of the laser pulse, the material structure is canceled within a small volume, the cavitation bubble (also referred to as spot 16 in the following) permanently or for a period of time lasting at least until the end of the operating period. The use of a sharply focused femtosecond laser accordingly offers the most precise localization of the laser action. In the sharply defined focus volume, the material structure is accordingly destroyed while no change in the material takes place in general in the closely adjacent areas (distance of less than one micrometer). This results in a high working precision while avoiding damage to neighboring regions of material.

For cuts and structuring, a large number of individual spots which dissolve the material structure are placed close to one another. The distance between adjacent spots should be on the order of the spot diameter at the end of the procedure. In FIG. 3a, a predetermined volume (e.g., a bore hole in the material) is generated by completely filling the volume to be removed with individual spots 16. In a nontransparent material of this kind, one proceeds by layers beginning with the layer of spots facing the laser.

In FIG. 3b, only the edge of the bore hole is covered by spots. In this case, a cut is shown through the material. The spots 16 should be arranged in a rotationally symmetric manner around the axis Z shown in dashes. In this way, a drill core is generated in the middle of the material 90 to be worked. The drill core can be removed subsequently as a cohesive piece. The required quantity of laser pulses is accordingly considerably reduced compared to FIG. 3a particularly in large cross-sectional surfaces of the bore hole.

An undercut in a transparent material 90 is shown in FIG. 3c. Since the radiation is not absorbed by the material 90, cohesive pieces of material can be detached from the material by placing the spots on the edge of the cut when this material adjoins the surface.

FIG. 3d shows how voids or structures (e.g., changes in the optical characteristics) can be generated depending upon the makeup of the material.

For macroscopic cut shapes (in the centimeter range), several million laser spots are required just to cover only the cut surface (FIGS. 3b and 3c) with spots in a sufficient density. For many applications (particularly medical applications), it is advantageous to keep the working time or treatment time as short as possible. Therefore, according to the invention, the radiation source of the laser device is capable of delivering laser pulses with a high repetition rate. FIG. 4 shows a schematic section of a possible scan pattern in which the individual spots 16 worked by individual laser pulses are arranged along paths which can be traveled by the scanner in a continuous manner. In order to achieve a sufficiently great distance between spots at high repetition rates of the radiation source 11, the focus is moved very fast in at least one of three scanning dimensions. The scan algorithms are therefore preferably designed in such a way that the spots are placed along paths which correspond to the natural movements of the deflection unit. The movement in the other two dimensions can then be carried out relatively slowly. The natural paths of the deflection unit can be, e.g., circular paths which the deflection units can travel at fixed rotational frequencies. This can be carried out, e.g., by rotating optical elements in the deflection unit. The radius of the circular path and the depth of focus (Z-direction) are then the gradually variable scan quantities. This variant is particularly suitable when rotationally symmetric cut shapes must be generated. The repetition rate of the laser can then be put to particularly effective use when the rotational frequency of the circular paths is selected in such a way that the full repetition rate of the radiation source leads to the desired spot distance d in the largest circular paths (B) to be traveled. When the circular paths are smaller in radius (A) when traveling over the cut pattern, the repetition rate of the source can be correspondingly reduced, resulting again in the optimal spot distance. This adaptation of the repetition rate can easily be achieved with the laser radiation source described above. Adapting the rotational frequency to the repetition rate of the source can be more difficult in technical respects, particularly when this is carried out continuously for every circular path (A, B). However, for purposes of reducing the working time, it can be advantageous to adapt the rotational frequency to the smaller circular paths in a few steps.

In FIG. 5, possible sequences of laser pulses are shown in and outside an oscillator-amplifier arrangement. The rotational frequency of the laser pulses in the oscillator 40 depend only on the resonator length and is predetermined for a determined radiation source and is around 100 MHz with resonator lengths of a few meters. With the regenerative amplification shown here, the pulses 41 are coupled into the amplifier and amplified, for example. When a lower repetition rate is desired, the amplification of the pulses 43 is carried out. The repetition rate of the amplified laser pulses is changed in an economical manner in this way.

Figure 6:
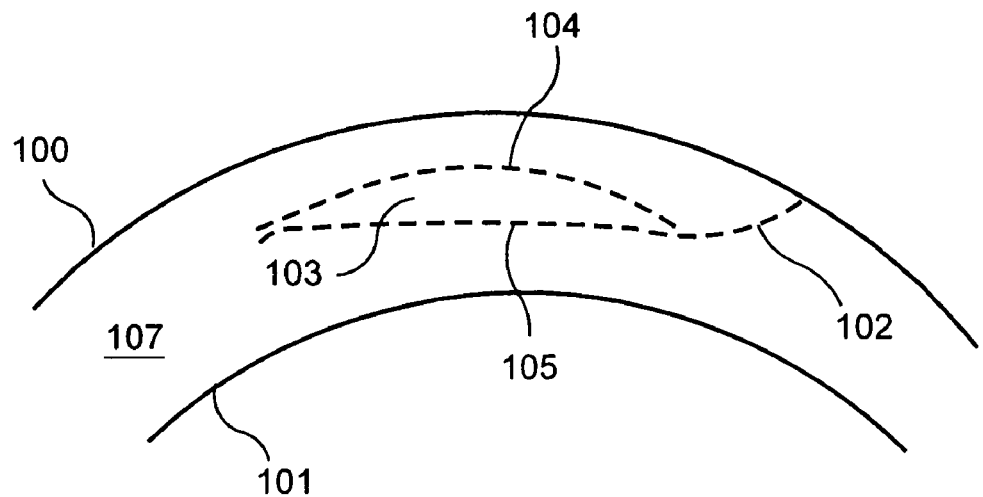
FIG. 6 shows the cutting control for generating a lenticle in section through the cornea.
Figure 7:
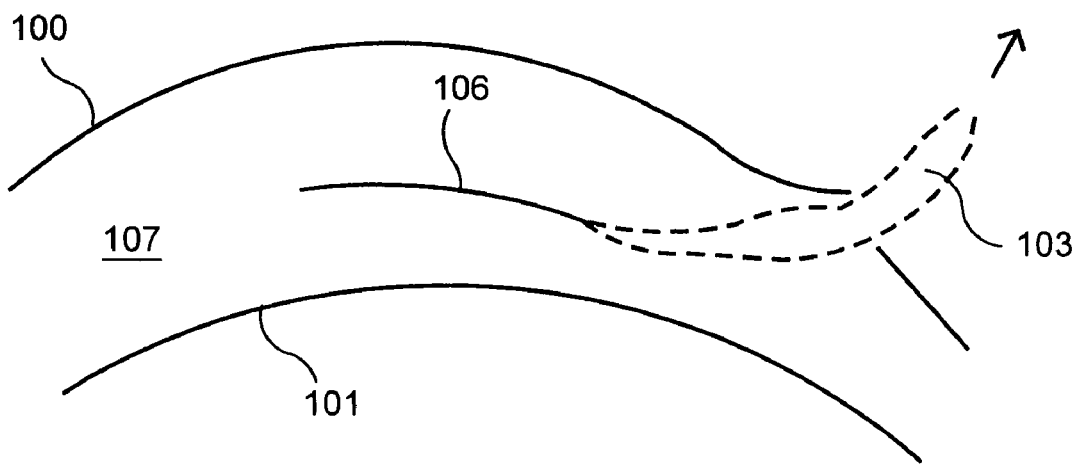
FIG. 7 shows the process of extracting the cut lenticle through a small lateral cut.

FIG. 6 shows a cut in the human cornea 107 with front side 100 and back side 101. The lenticle 103 is formed by the two surface cuts 104 and 105. A small lateral cut 102 which leads as far as the front surface 100 of the cornea makes it possible to extract the lenticle 103. This extraction is shown in FIG. 7. The remaining void collapses 106.

FIG. 8 shows the cornea in a top view. The border 111 of the lenticle 103 and the cuts 102 leading to the front surface of the cornea are shown in the drawing. The front surface of the cornea is severed along line 110 and makes it possible to extract the lens.

FIG. 9 shows another preferred form of making the cut. The lenticle is divided into two parts 123 ad 124 by a cut 122. Instead of an individual extraction cut 110, two extraction cuts 120 and 121 are made. Subsequently, the lens part 123 is removed through the extraction cut 120 and the lens part 124 is removed through the extraction cut 121.

FIG. 10 shows another expression of the method according to the invention. In this case, the lenticle bordered by the edge 111 is cut into many small fragments 132. These fragments 132 can now be sucked out by means of a cannula 133 which preferably has a diameter that is adapted to the fragment size. This process can be reinforced by a rinsing device via a second cannula 134 which is introduced into an oppositely located duct or even the same duct. The rinsing medium 136, 135 is preferably isotonic saline solution, but other solutions can also be used. This process achieves the minimum weakening of the cornea through these methods of refractive laser surgery.

The invention was described with reference to preferred embodiment examples. Further developments carried out by persons skilled in the art do not constitute a departure from the protective scope defined by the claims.

While the foregoing description and drawings represent the present invention, it will be obvious to those skilled in the art that various changes may be made therein without departing from the true spirit and scope of the present invention.

The invention claimed is:

1. A method for precise working of material, particularly organic tissue, comprising the step of providing laser pulses with a pulse length between 50 fs and 1 ps and with a pulse frequency greater than 100 kHz, up to 500 kHz, and with a wavelength between 600 and 2000 nm for acting on the material to be worked;

wherein the laser pulses are focused on or in the material and the focal points are guided in three dimensions;

wherein the focus points are guided in such a way so as to generate a first cut surface in the material;

wherein the first cut surface is a flat or three-dimensional cohesive cut surface; and wherein a plurality of laser spots are placed close to one another at the edge of the cut in the material, and the spots are arranged in a rotationally symmetric manner around a z-axis.

2. The method for precise working of material according to claim 1;
wherein the z-axis is perpendicular to a surface of the material.

3. The method for precise working of material according to claim 1;
wherein a second cut surface is generated in the material and, together with the first cut surface, surrounds an essentially lens-shaped severed portion of material.

4. The method for precise working of material according to claim 3;
wherein additional cut surfaces are generated in the severed portion of material.

5. The method for precise working of material according to claim 3;
wherein at least one cut is generated between the material surface and the severed portion of material.

6. The method for precise working of material according to claim 5;
wherein the severed portion of material is extracted from the material through the at least one cut.

7. The method for precise working of material according to claim 6;
wherein the material portion is divided into small fragments and the extraction of these fragments is carried out by a suction/rinsing device.

8. The method for precise working of material according to claim 1;
wherein the energy of the individual pulses is between about 100 nJ and 5 µJ.

9. The method for precise working of material according to claim 1;
wherein the time interval between the laser pulses is varied depending upon the location of the focus point.

10. The method for precise working of material according to claim 1;
wherein the speed at which the focus points are guided is varied depending upon the location of the focus points.

11. A method for precise working of material, particularly organic tissue, comprising the step of providing laser pulses with a pulse length between 50 fs and 1 ps and with a pulse frequency from 300 kHz to 1 MHz and with a wavelength between 600 and 2000 nm for acting on the material to be worked;
wherein the laser pulses are focused on or in the material and the focal points are guided in three dimensions;
wherein the focus points are guided in such a way so as to generate a first cut surface in the material; and
wherein the first cut surface is a flat or three-dimensional cohesive cut surface.

12. The method for precise working of material according to claim 11;
wherein the pulse frequency is in the range of from 500 kHz to 1 MHz.

13. The method for precise working of material according to claim 11;
wherein a second cut surface is generated in the material and, together with the first cut surface, surrounds an essentially lens-shaped severed portion of material.

14. The method for precise working of material according to claim 13;
wherein additional cut surfaces are generated in the severed portion of material.

15. The method for precise working of material according to claim 13;
wherein at least one cut is generated between the material surface and the severed portion of material.

16. The method for precise working of material according to claim 15;
wherein the severed portion of material is extracted from the material through the at least one cut.

17. The method for precise working of material according to claim 16;
wherein the material portion is divided into small fragments and the extraction of these fragments is carried out by a suction/rinsing device.

18. The method for precise working of material according to claim 11;
wherein the energy of the individual pulses is between about 100 nJ and 5 µJ.

19. The method for precise working of material according to claim 11;
wherein the time interval between the laser pulses is varied depending upon the location of the focus point.

20. The method for precise working of material according to claim 11;
wherein the speed at which the focus points are guided is varied depending upon the location of the focus points.

* * * * *